US012765959B2

(12) United States Patent
Loschak et al.

(10) Patent No.: US 12,765,959 B2
(45) Date of Patent: Oct. 20, 2026

(54) SURGICAL ROBOTIC SYSTEM SETUP USING COLOR CODING

(71) Applicant: Covidien LP, Mansfield, MA (US)

(72) Inventors: Paul M. Loschak, Somerville, MA (US); William J. Peine, Ashland, MA (US); Jaimeen V. Kapadia, Cambridge, MA (US); Dustin C. Eastman, Longmont, CO (US); Colin H. Murphy, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 264 days.

(21) Appl. No.: 18/686,571

(22) PCT Filed: Aug. 23, 2022

(86) PCT No.: PCT/IB2022/057905
§ 371 (c)(1),
(2) Date: Feb. 26, 2024

(87) PCT Pub. No.: WO2023/026199
PCT Pub. Date: Mar. 2, 2023

(65) Prior Publication Data

US 2025/0127577 A1 Apr. 24, 2025

Related U.S. Application Data

(60) Provisional application No. 63/237,705, filed on Aug. 27, 2021.

(51) Int. Cl.
*A61B 34/37* (2016.01)
*A61B 17/00* (2006.01)
(Continued)

(52) U.S. Cl.
CPC .............. *A61B 34/37* (2016.02); *A61B 17/00* (2013.01); *A61B 34/25* (2016.02); *A61B 50/13* (2016.02);
(Continued)

(58) Field of Classification Search
CPC ......... A61B 34/37; A61B 50/13; A61B 90/92; A61B 34/25
See application file for complete search history.

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |

(Continued)

FOREIGN PATENT DOCUMENTS

| | | | |
|---|---|---|---|
| EP | 3505129 | A1 | 7/2019 |
| WO | 2019204013 | A1 | 10/2019 |
| WO | 2021247294 | A1 | 12/2021 |

OTHER PUBLICATIONS

Bottone Giacinto, “Minimal-invasive Chirurgie und Operationsroboter für Krankenhäuser in aller Welt—Innovation Origins”, May 20, 2020 (May 20, 2020), p. 1-8, Retrieved from the Internet: <URL:https://innovationorigins.com/de/minimal-invasive-chirurgie-und-operationsroboter-fuer-krankenhaeuser-in-aller-welt/> XP055982386. The photograph on p. 1.

(Continued)

*Primary Examiner* — Carl H Layno
*Assistant Examiner* — Bryan Mcallister Lee
(74) *Attorney, Agent, or Firm* — Carter, DeLuca & Farrell, LLP

(57) ABSTRACT

A surgical robotic system having multiple robotic arm carts includes color indicator lights. The same colors are used to represent various elements on a graphical user interface to
(Continued)

allow for easy identification and correlation between GUI elements and the robotic arm carts.

20 Claims, 7 Drawing Sheets

(51) Int. Cl.
*A61B 34/00* (2016.01)
*A61B 50/13* (2016.01)
*A61B 90/92* (2016.01)

(52) U.S. Cl.
CPC ..... *A61B 90/92* (2016.02); *A61B 2017/00115* (2013.01); *A61B 2017/00973* (2013.01)

(56) References Cited

U.S. PATENT DOCUMENTS

| | | | |
|---|---|---|---|
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,170,717 | B2 | 5/2012 | Sutherland et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |

(56) References Cited

U.S. PATENT DOCUMENTS

| | | | |
|---|---|---|---|
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,852,174 | B2 | 10/2014 | Burbank |
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |

(56) References Cited

U.S. PATENT DOCUMENTS 10,813,710 B2 10/2020 Grubbs
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.
10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.
10,993,773 B2 5/2021 Cooper et al.
10,993,775 B2 5/2021 Cooper et al.
11,000,331 B2 5/2021 Krom et al.
11,013,567 B2 5/2021 Wu et al.
11,020,138 B2 6/2021 Ragosta
11,020,191 B2 6/2021 Diolaiti et al.
11,020,193 B2 6/2021 Wixey et al.
11,026,755 B2 6/2021 Weir et al.
11,026,759 B2 6/2021 Donlon et al.
11,040,189 B2 6/2021 Vaders et al.
11,045,077 B2 6/2021 Stern et al.
11,045,274 B2 6/2021 Dachs, II et al.
11,058,501 B2 7/2021 Tokarchuk et al.
11,076,925 B2 8/2021 DiMaio et al.
11,090,119 B2 8/2021 Burbank
11,096,687 B2 8/2021 Flanagan et al.
11,098,803 B2 8/2021 Duque et al.
11,100,430 B1 * 8/2021 Neumann ............... G06F 18/22
11,109,925 B2 9/2021 Cooper et al.
11,116,578 B2 9/2021 Hoffman et al.
11,129,683 B2 9/2021 Steger et al.
11,135,029 B2 10/2021 Suresh et al.
11,147,552 B2 10/2021 Burbank et al.
11,147,640 B2 10/2021 Jarc et al.
11,154,373 B2 10/2021 Abbott et al.
11,154,374 B2 10/2021 Hanuschik et al.
11,160,622 B2 11/2021 Goldberg et al.
11,160,625 B2 11/2021 Wixey et al.
11,161,243 B2 11/2021 Rabindran et al.
11,166,758 B2 11/2021 Mohr et al.
11,166,770 B2 11/2021 DiMaio et al.
11,166,773 B2 11/2021 Ragosta et al.
11,173,597 B2 11/2021 Rabindran et al.
11,185,378 B2 11/2021 Weir et al.
11,191,596 B2 12/2021 Thompson et al.
11,197,729 B2 12/2021 Thompson et al.
11,213,360 B2 1/2022 Hourtash et al.
11,221,863 B2 1/2022 Azizian et al.
11,234,700 B2 2/2022 Ragosta et al.
11,241,274 B2 2/2022 Vaders et al.
11,241,290 B2 2/2022 Waterbury et al.
11,259,870 B2 3/2022 DiMaio et al.
11,259,884 B2 3/2022 Burbank
11,272,993 B2 3/2022 Gomez et al.
11,272,994 B2 3/2022 Saraliev et al.
11,291,442 B2 4/2022 Wixey et al.
11,291,513 B2 4/2022 Manzo et al.
11,376,002 B2 7/2022 Shelton, IV et al.
11,376,098 B2 7/2022 Shelton, IV et al.
11,381,759 B2 7/2022 Zhao et al.
11,382,621 B2 7/2022 Scheib et al.
11,382,624 B2 7/2022 Harris et al.
11,382,625 B2 7/2022 Huitema et al.
11,382,626 B2 7/2022 Shelton, IV et al.
11,382,627 B2 7/2022 Huitema et al.
11,382,638 B2 7/2022 Harris et al.
11,382,644 B2 7/2022 Schoettgen et al.
11,389,160 B2 7/2022 Shelton, IV et al.
11,389,255 B2 7/2022 DiMaio et al.
11,399,906 B2 8/2022 Shelton, IV et al.
11,406,379 B2 8/2022 Hess et al.
11,410,259 B2 8/2022 Harris et al.
11,419,630 B2 8/2022 Yates et al.
11,424,027 B2 8/2022 Shelton, IV
11,432,888 B2 9/2022 Diolaiti et al.
11,432,893 B2 9/2022 Itkowitz et al.
11,432,895 B2 9/2022 Loh et al.
11,439,390 B2 9/2022 Patel et al.
11,439,391 B2 9/2022 Bruns et al.
11,468,791 B2 10/2022 Jarc et al.
11,471,155 B2 10/2022 Shelton, IV et al.
11,471,221 B2 10/2022 Zhao et al.
11,478,308 B2 10/2022 Hoffman et al.
11,490,977 B2 11/2022 Schena et al.
11,497,499 B2 11/2022 Shelton, IV et al.
11,504,119 B2 11/2022 Shelton, IV et al.
11,504,124 B2 11/2022 Patel et al.
11,510,743 B2 11/2022 Shelton, IV et al.
11,517,312 B2 12/2022 Wixey
11,517,325 B2 12/2022 Shelton, IV et al.
11,518,048 B2 12/2022 Saraliev et al.
2007/0142824 A1 * 6/2007 Devengenzo .......... A61B 34/30
606/1
2014/0055489 A1 * 2/2014 Itkowitz ................. A61B 34/37
345/633
2020/0306997 A1 10/2020 Koenig et al.
2020/0405420 A1 12/2020 Purohit et al.
2021/0212776 A1 7/2021 Schmitt et al.

OTHER PUBLICATIONS

Cmr Surgical, "Introducing Versius, CMR Surgical", Jan. 11, 2019 (Jan. 11, 2019), Retrieved from the Internet: <URL: https://www.youtube.com/watch?v=a9mXmmhMKqY> XP055982318.
Shin Brian C. et al., "Do Illuminated Foot Pedals Improve the Speed and Accuracy of Pedal Activation During Endoscopic Procedures?", Journal of Endourology, vol. 32, No. 7, Jul. 1, 2018 (Jul. 1, 2018), pp. 653-658, XP055982412.
International Search Report and Written Opinion of the International Searching Authority issued in corresponding application PCT/IB2022/057905 mailed Nov. 24, 2022 (13 pages).
International Preliminary Report on Patentability issued in corresponding International Application No. PCT/IB2022/057905 issued Feb. 27, 2024, 10 pages.

* cited by examiner

SURGICAL ROBOTIC SYSTEM SETUP USING COLOR CODING

CROSS REFERENCE TO RELATED APPLICATIONS

The present application is a U.S. National Stage Application filed under 35 U.S.C. § 371(a) of International Patent Application No. PCT/IB2022/057905, filed on Aug. 23, 2022, which claims the benefit of and priority to U.S. Patent Provisional Application No. 63/237,705, filed on Aug. 27, 2021. The entire disclosures of the foregoing applications are incorporated by reference herein.

BACKGROUND

Technical Field

The present disclosure generally relates to the optimization and improvement of surgical robotic systems having one or more modular movable carts each of which supports a robotic arm, and a surgeon console for controlling the carts and their respective arms. In particular, the present disclosure relates to a system and method of registering a plurality of arm carts on a graphical user interface displayed on a surgeon interactive display using a color-coded scheme.

Background of Related Art

Surgical robotic systems are currently being used in minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

While performing surgical procedures with multiple robotic arms that are supported on untethered movable surgical carts the relative positioning and operational status of each robotic arm can be difficult for users to associate with the actual surgical cart. Thus, there is a need to provide clinicians with easily decipherable accurate real-time information about the relative positioning and operational status of each robotic arm of the surgical robotic system.

SUMMARY

According to one embodiment of the present disclosure, a surgical robotic system is disclosed. The surgical robotic system includes a plurality of movable carts each of which may include a robotic arm and a cart color indicator configured to display a unique color. The system may also include a surgeon console having: a display configured to display a graphical user interface having a plurality of graphical representations each of which corresponds to one movable cart of the plurality of movable carts. Each of the graphical representations displays the unique color of the cart color indicator of the corresponding movable cart and a plurality of foot pedals configured to control the robotic arms. Each of the plurality of foot pedals may include a pedal color indicator, where each of the pedal color indicators may be configured to display the unique color of the cart color indicator of a movable cart based on a foot pedal assignment.

Implementations of the above embodiment may include one or more of the following features. According to one aspect of the above embodiment, each of the cart color indicator and the pedal color indicator may include at least one light emitting diode. The system may also include a control tower configured to control the robotic arm of each movable cart of the plurality of movable carts based on a user input received at the surgeon console. The control tower may be configured to assign the unique color to each of the cart color indicators. The control tower may be also configured to assign the unique color to each of the cart color indicators based on a user selection. The display may be a touchscreen and each graphical representation of the plurality of graphical representations may be movable on the touchscreen.

According to another embodiment of the present disclosure, a surgical robotic system is disclosed. The surgical robotic system may include a plurality of movable carts each of which may include a robotic arm and a cart color indicator configured to display a unique color. The system may also include a surgeon console having a display configured to display a graphical user interface having a plurality of graphical representations, each of which corresponds to one movable cart of the plurality of movable carts, where each of the graphical representations displays the unique color of the cart color indicator of the corresponding movable cart.

Implementations of the above embodiment may include one or more of the following features. According to one aspect of the above embodiment, the cart color indicator may include at least one light emitting diode. The surgeon console further may include a plurality of foot pedals configured to control the robotic arms. Each of the plurality of foot pedals may include a pedal color indicator. Each of the pedal color indicators may be configured to display the unique color of the cart color indicator of a movable cart based on a foot pedal assignment. The pedal color indicator may include at least one light emitting diode. The controller may be configured to control the robotic arm of each movable cart of the plurality of movable carts based on a user input received at the surgeon console. The controller may be configured to assign the unique color to each of the cart color indicators. The controller may be configured to assign the unique color to each of the cart color indicators based on a user selection. The display may be a touchscreen and each graphical representation of the plurality of graphical representations may be movable on the touchscreen.

According to a further embodiment of the present disclosure, a method for controlling a surgical robotic system is disclosed. The method may include selecting a unique color for each cart color indicator of a movable cart of a plurality of movable carts. The method may also include outputting on a display of a surgeon console a graphical user interface may include a plurality of graphical representations each of which corresponds to one movable cart of the plurality of movable carts, where each of the graphical representations displays the unique color of the cart color indicator of the corresponding movable cart.

Implementations of the above embodiment may include one or more of the following features. According to one aspect of the above embodiment, the method may also include assigning at one or more pedals to each robotic arm, each of which is disposed on one movable cart of the plurality of carts. The method may further include displaying on a pedal color indicator the unique color of the cart color indicator of a movable cart based on a foot pedal assignment.

BRIEF DESCRIPTION OF THE DRAWINGS

Various aspects of the present disclosure are described herein with reference to the drawings wherein.

DETAILED DESCRIPTION

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

Figure 1:
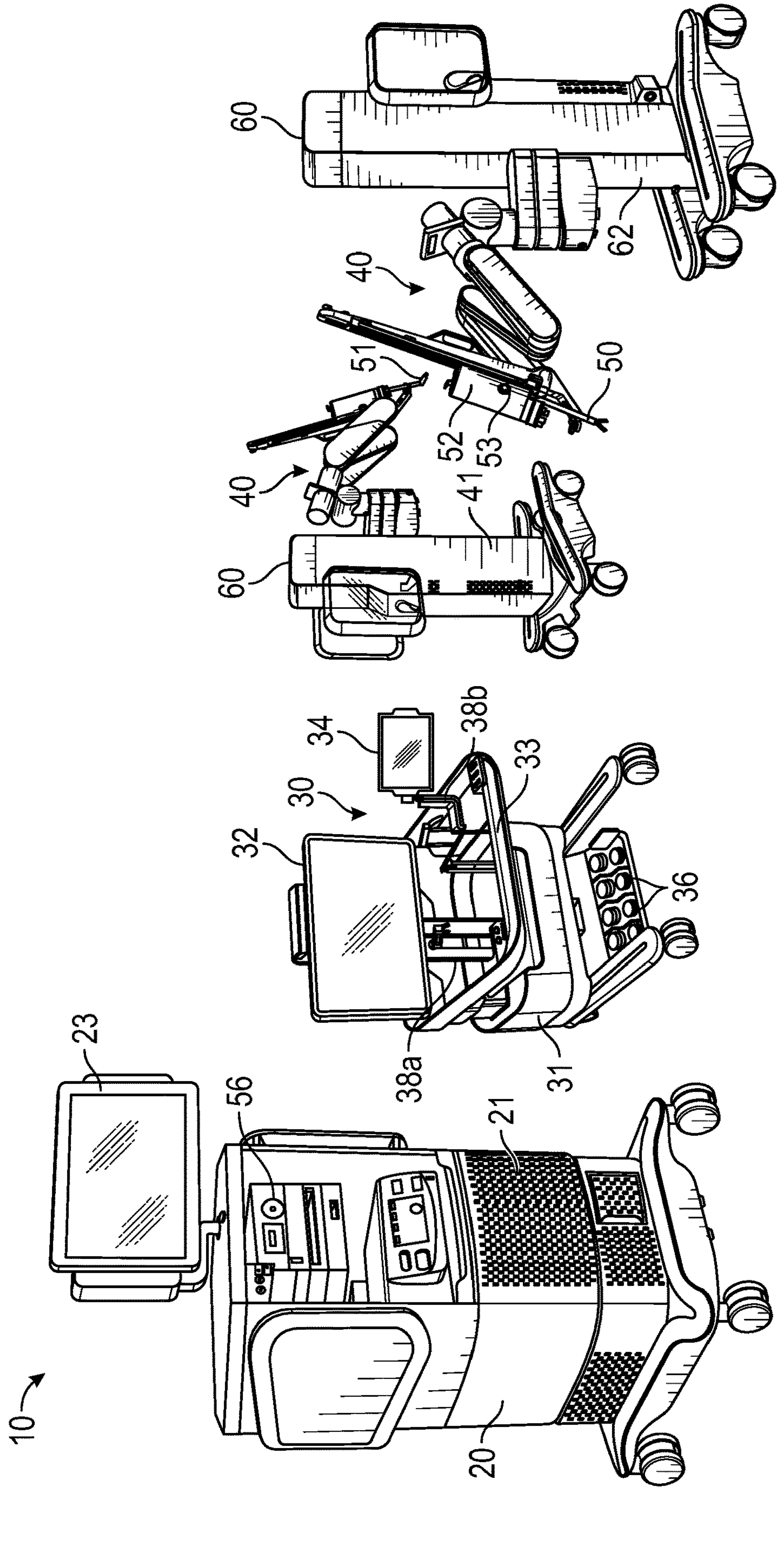
FIG. 1 is a schematic illustration of a surgical robotic system including a control tower, a console, and one or more surgical robotic arms each disposed on a movable cart according to an aspect of the present disclosure.

With reference to FIG. 1, a surgical robotic system 10 includes a control tower 20, which is connected to all of the components of the surgical robotic system 10 including a surgeon console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In aspects, the surgical instrument 50 may be configured for open surgical procedures. In aspects, the surgical instrument 50 may be an endoscope, such as an endoscopic camera 51, configured to provide a video feed for the user. In further aspects, the surgical instrument 50 may be an electrosurgical forceps configured to seal tissue by compressing tissue between jaw members and applying electrosurgical current thereto. In yet further aspects, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 perform the image processing based on the depth estimating algorithms of the present disclosure and output the processed video stream.

The surgeon console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs. The video processing device 56 is configured to process the video feed from the endoscopic camera 51 and to output a processed video stream on the first displays 32 of the surgeon console 30 and/or the display 23 of the control tower 20.

The surgeon console 30 also includes a plurality of user interface devices, such as foot pedals 36 and a pair of handle controllers 38*a* and 38*b* which are used by a user to remotely control robotic arms 40. The surgeon console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38*a* and 38*b*.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
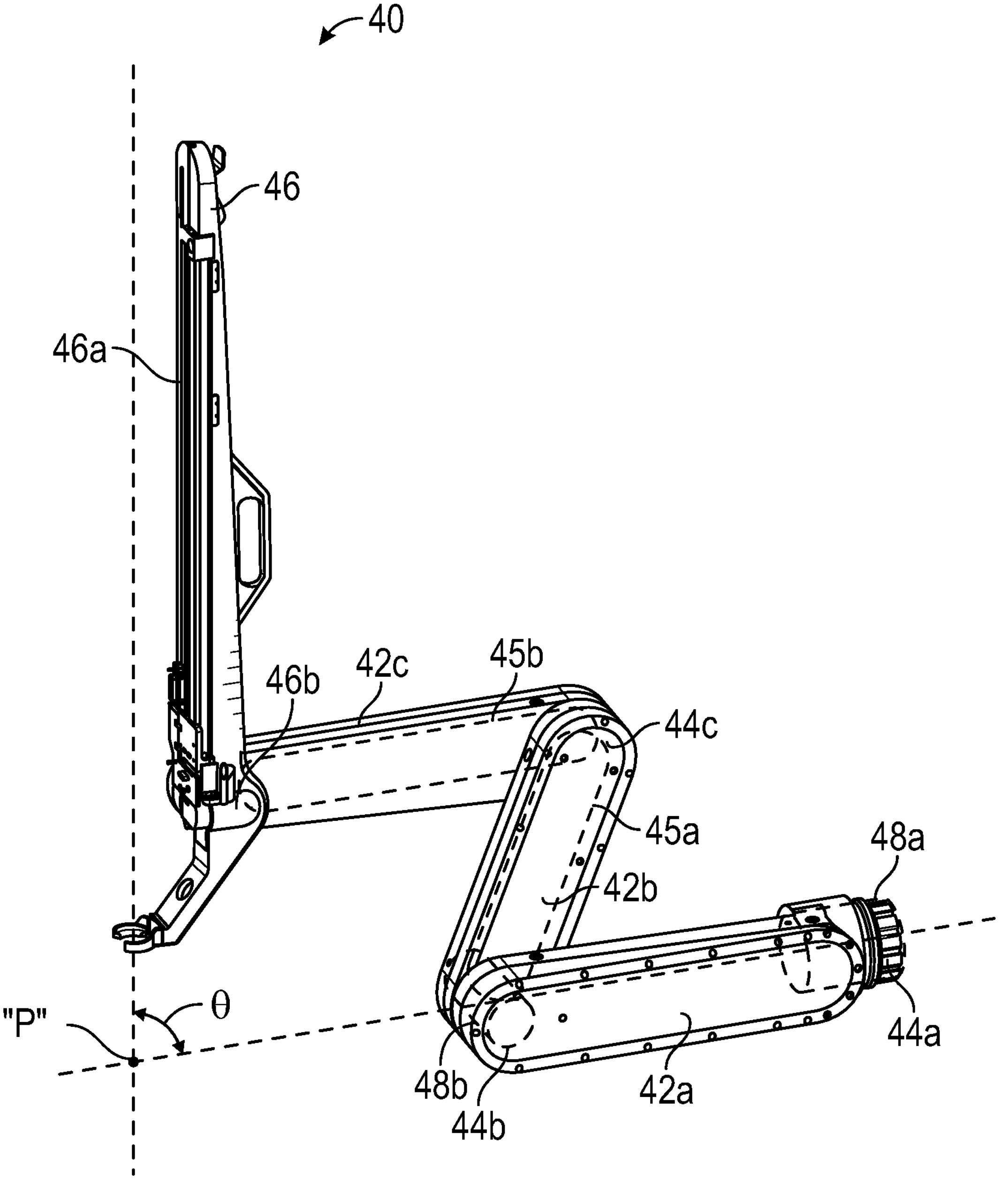
FIG. 2 is a perspective view of a surgical robotic arm of the surgical robotic system of FIG. 1 according to an aspect of the present disclosure.
Figure 3:
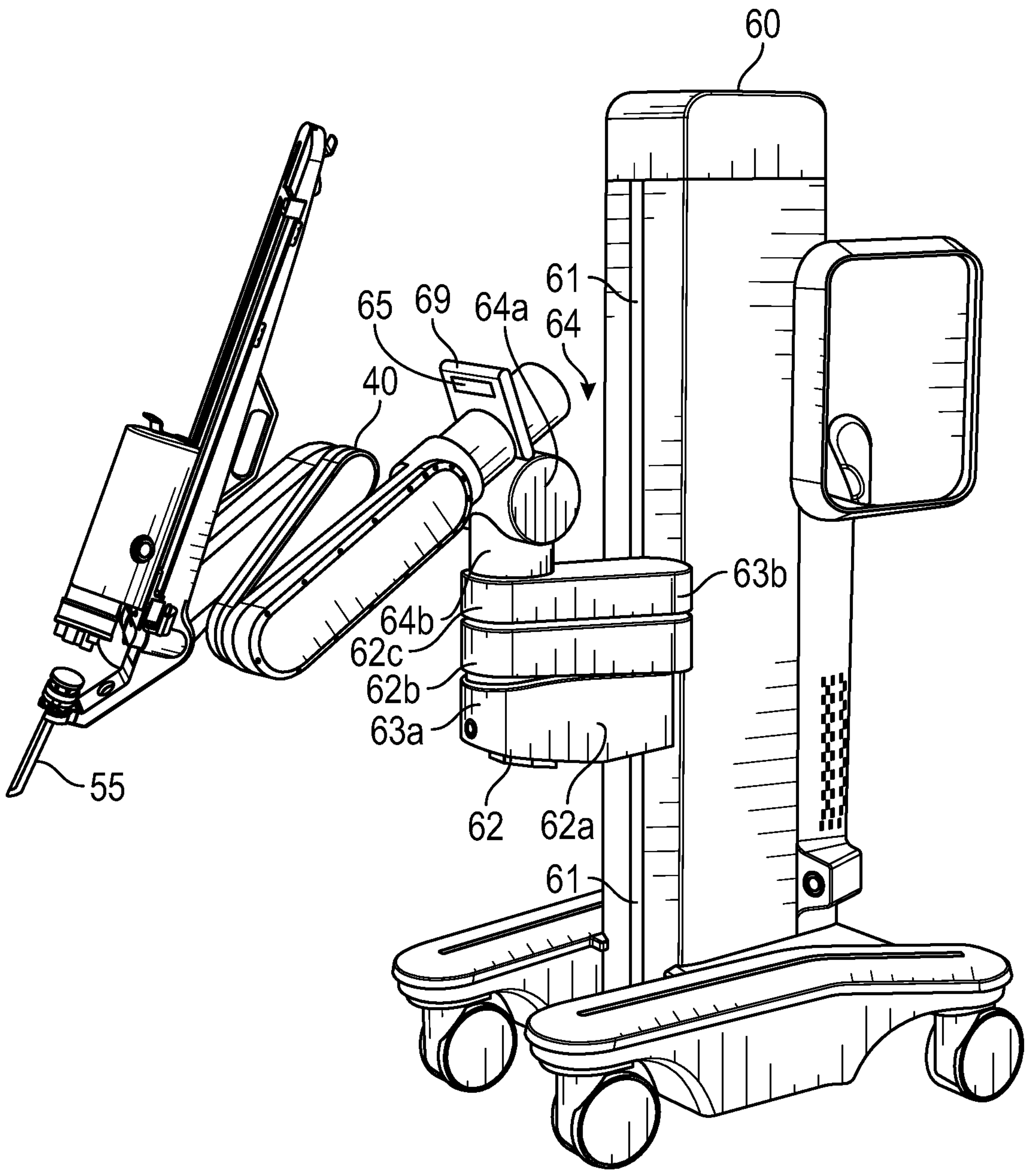
FIG. 3 is a perspective view of a setup arm with the surgical robotic arm of the surgical robotic system of FIG. 1 according to an aspect of the present disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

Figure 5:
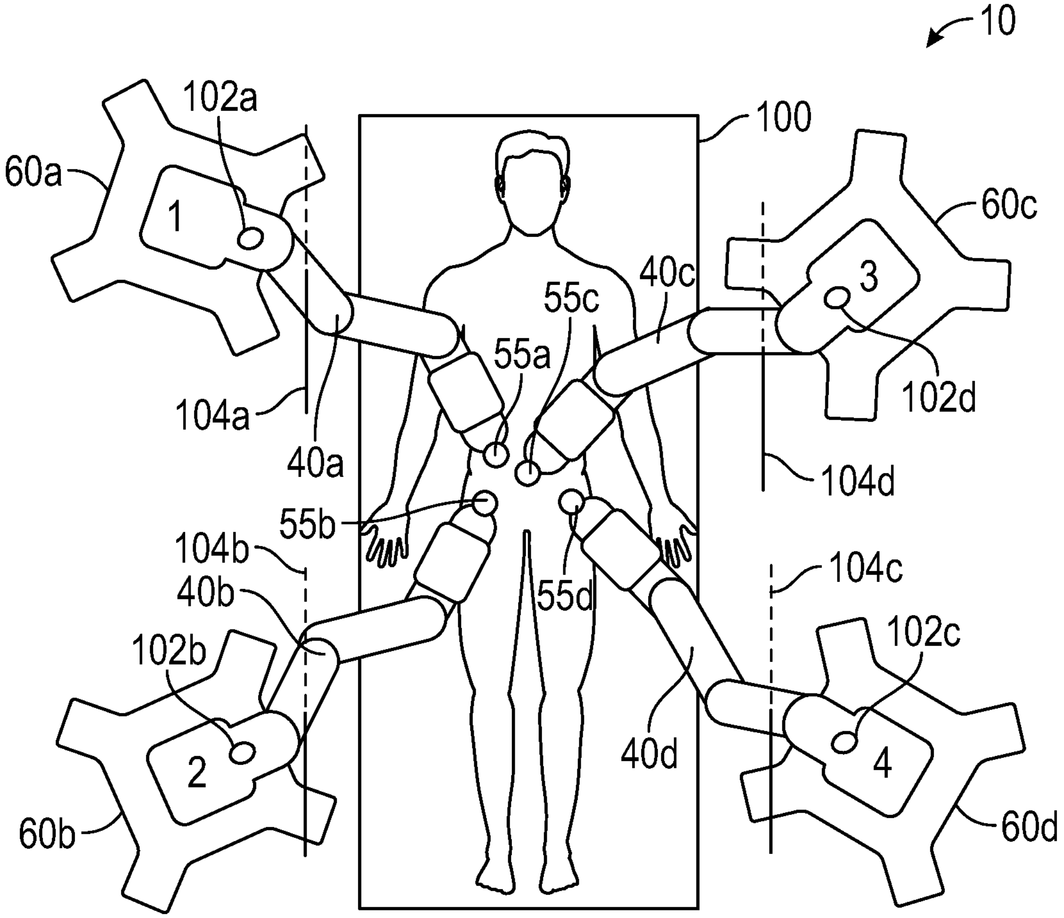
FIG. 5 is a plan schematic view of movable carts of FIG. 1 positioned about a surgical table according to an aspect of the present disclosure.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In aspects, the robotic arm 40 may be coupled to a surgical table 100 (FIG. 5). The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*c* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In aspects, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
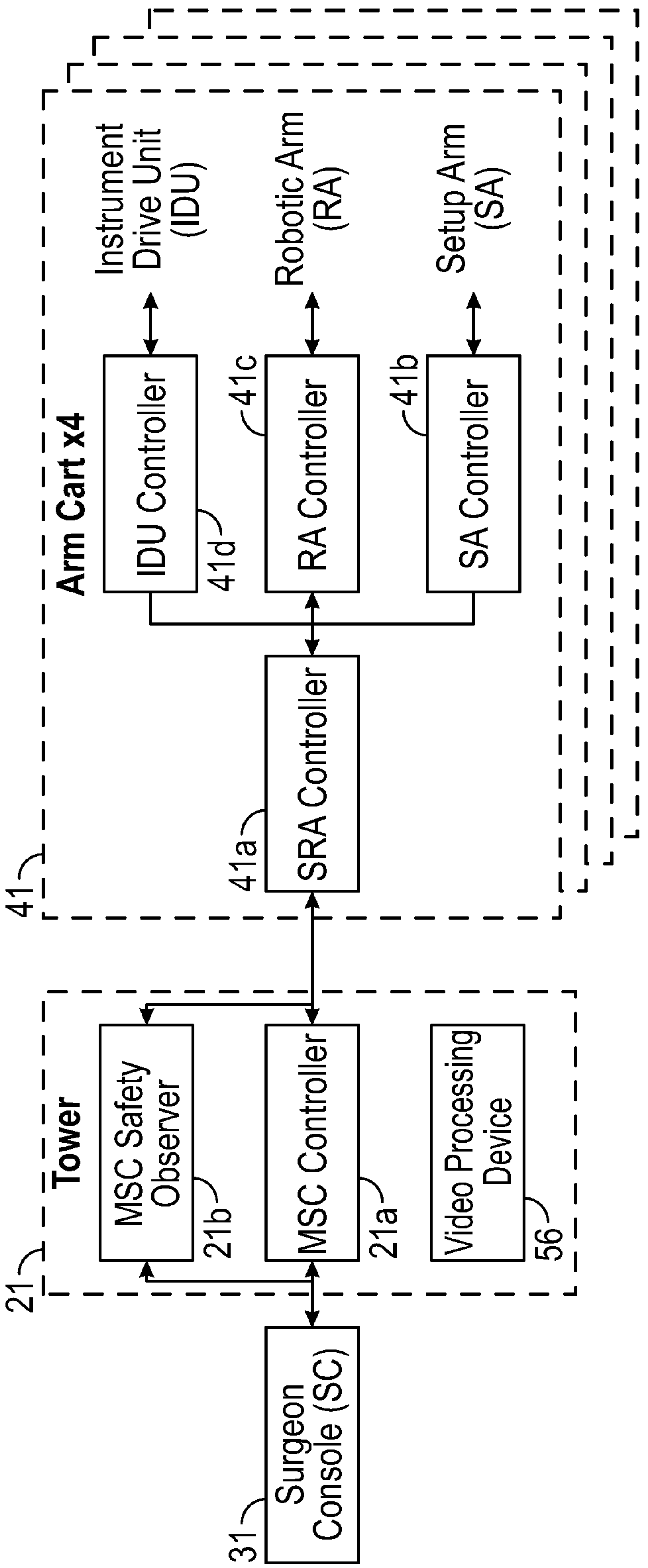
FIG. 4 is a schematic diagram of a computer architecture of the surgical robotic system of FIG. 1 according to an aspect of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

The setup arm controller 41*b* controls each of joints 63*a* and 63*b*, and the rotatable base 64 of the setup arm 62 and calculates desired motor movement commands (e.g., motor torque) for the pitch axis and controls the brakes. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and role-pitch-yaw ("RPY") orientation relative to a coordinate reference frame, which is fixed to the surgeon console 30. The desired pose of the instrument 50 is relative to a fixed frame on the robotic arm 40. The pose of the handle controller 38*a* is then scaled by a scaling function executed by the controller 21*a*. In aspects, the coordinate position is scaled down and the orientation is scaled up by the scaling function. In addition, the controller 21*a* also executes a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

With reference to FIG. 5, the surgical robotic system 10 is setup around the surgical table 100. The system 10 includes movable carts 60*a-d*, which may be numbered "1" through "4." Each of the carts 60*a-d* also includes a unique color allowing for easy identification by operating room's personnel. In embodiments, the carts 60*a-d* may have a color indicator 102*a-d*, which may include one or more LEDs disposed in any suitable pattern or shape (e.g., a circle, a bar, etc.) The color indicators 102*a-d* may be disposed on any component of the carts 60*a-d*, such as the robotic arm 40, the top of the cart, the base, etc. In embodiments, multiple color indicators 102*a-d* may be used on each of the movable carts 60*a-d*, allowing for different color indicators 102*a-d* to be used to display specific statuses pertaining to the movable cart 60*a-d* and associated robotic arm 40. Thus, one of the color indicators 102*a-d* may be used to indicate the mode while another is used to identify the movable cart 60*a-d*. In further embodiments, the color indicators 102*a-d* may also be disposed on the instrument 50 and/or the IDU 52. Color indicators 102*a-d* may be LED strips disposed along the robotic arms 40*a-d* and movable carts 60*a-d*.

During setup, each of the carts 60*a-d* are positioned around the surgical table 100. Position and orientation of the carts 60*a-d* depends on a plurality of factors, such as placement of a plurality of ports 55*a-d*, which in turn, depends on the surgery being performed. Once the port placement is determined, the ports 55*a-d* are inserted into the patient, and carts 60*a-d* are positioned to insert instruments 50 and the endoscopic camera 51 into corresponding ports 55*a-d*. Orientation of the carts 60*a-d* and their corresponding robotic arms 40*a-d* may be based on individual laser alignment patterns 104*a-d*. For a more detailed description of using alignment patterns to orient a plurality of movable carts 60 see International Application No. PCT/US2021/034125, titled "SURGICAL ROBOTIC SYSTEM USER INTERFACES", filed on May 26, 2021, the entire disclosure of which is incorporated by reference herein.

Figure 6:
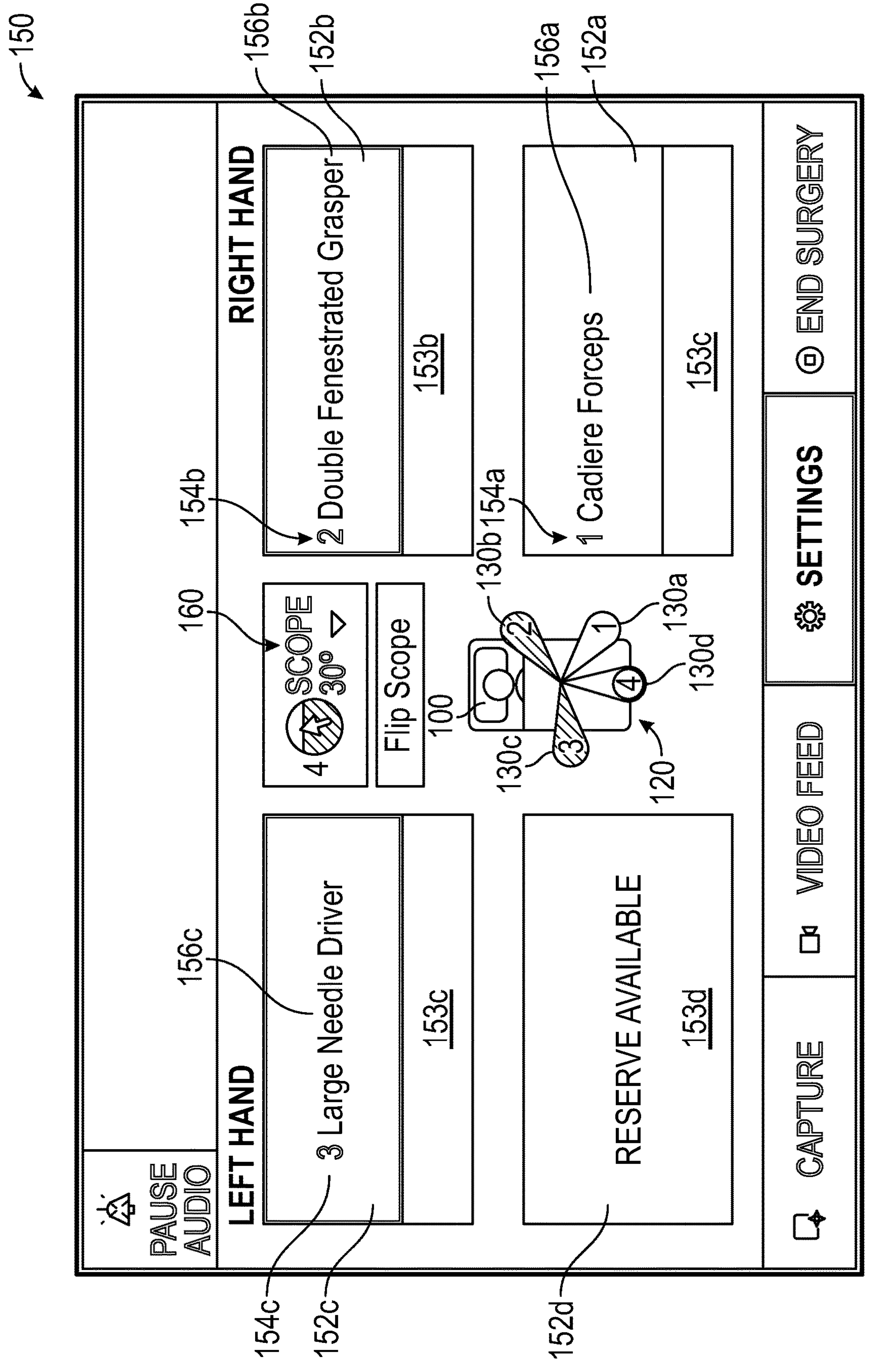
FIG. 6 is a graphical user interface displayed on a display of the surgeon console according to an embodiment of the present disclosure.
Figure 7:
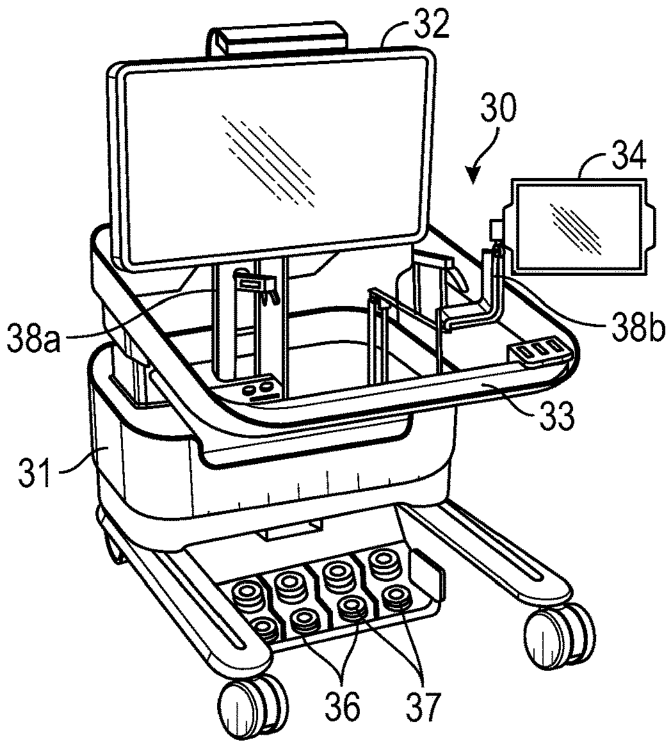
FIG. 7 is a perspective view the surgeon console of FIG. 1 according to an embodiment of the present disclosure.

Once the movable carts 60*a-d* are placed at their desired positions, the surgeon or any other personnel registers each of the robotic arms 40*a-d* on a graphical user interface (GUI) 150, which may be displayed on the second display 34 or any other display of the surgical robotic system 10, e.g., displays 23 or 32. With reference to FIG. 6, the surgeon supplementary user interface 150 includes a plurality of regions 153*a-d* which include graphical representations 152*a-c* for each of the three robotic arms 40*a-c*, which are numbered "1"-"3" and a reserve graphical representation 152*d*. Each of the graphical representations 152*a-c* includes an identification number 154*a-c* and an instrument type 156*a-c*. The user interface 150 also includes an orientation indicator 160. The orientation indicator 160 shows rotation and pitch indication of the camera 51, which shows rotation and pitch indication of the camera 51 that is coupled to the robotic arm 40*d* numbered "4". The arms 60*a-d* may be automatically assigned to each of the graphical representations 152*a-c*, with the graphical representations 152*a* and 152*b* being controlled by the right-hand controller 38*b* and the graphical representations 152*c* and 152*d* being controlled by the left-hand controller 38*a*. However, the surgeon may move the instruments 50, i.e., robotic arms 60*a-c* between any of the four graphical representations 152*a-d*.

To aid in registration of the robotic arms 40*a-d* and their associated instruments 50 and the camera 51, each of the graphical representations 152*a-c* and the orientation indicator 160 match the color of the color indicators 102*a-d*. Thus, the graphical representations 152*a-d* and the orientation indicator 160 adopt the color of the color indicators 102*a-d*. The GUI 150 also shows a bed map 120 showing a surgical table 100 and each of the robotic arms 40*a-d* represented as arrows 130*a-d*. Similar to the graphical representations 152*a-c*, the arrows 130*a-d* also match the color of the color indicators 102*a-d*.

As noted above, the second display 34 is a touchscreen, which allows for moving the graphical representations 152*a-d* between the regions 153*a-d* by pressing, holding, and moving or using any other suitable touch gesture, e.g., moving the graphical representation 152*a* from the region 153*a* to any of the other regions 153*b-d*. This assigns the instrument to a desired one of the hand controllers 38*a* and 38*b*, designated as "LEFT HAND" and "RIGHT HAND,"

respectively. As the icons are moved between any of the graphical representations 152*a-c*, the user can confirm the actual physical location of the instruments 50 and their corresponding robotic arms 40*a-d* by matching the colors displayed on the GUI 150 to the colors on the color indicators 102*a-d* regardless of which graphical representation 152*a-d* is being used.

In addition to color coding the GUI 150, the color indicators 102*a-d* may be also programmed to match the color of the foot pedals 36. Each of the robotic arms 40*a-d* may be controlled by a subset of the foot pedals 36. Each of the foot pedals 36 includes a color indicator 37, which may include one or more LEDs disposed in any suitable on or adjacent the foot pedals 36 (e.g., a ring). The number and which specific foot pedals 36 are assigned to each of the robotic arms 40*a-c* depends on the type of instrument 50 or endoscopic camera 51 attached to the robotic arms 40*a-d*. The controller 21*a* may automatically assign a subset of the foot pedals 36 to each of the robotic arms 40*a-d*. Once assigned, the color indicators 37 are lit up based on the color of the color indicators 102*a-d*.

Figure 8:
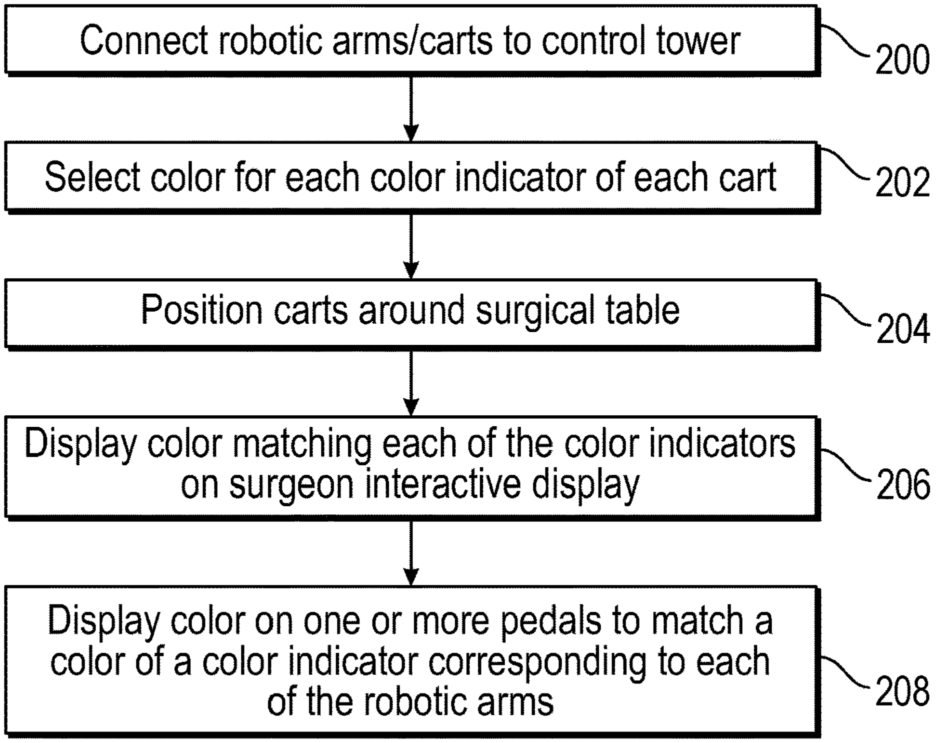
FIG. 8 is a flow chart of a method for configuring the surgical robotic system of FIG. 1 according to an embodiment of the present disclosure.

With reference to FIG. 8, a method of using color coding to register a plurality of movable carts 60*a-d* includes connecting each of the movable carts 60*a-d* to the control tower 20 to set the color for each of the color indicators 102*a-d* at step 200. The color of the color indicators 102*a-d* may be user-selectable during initial setup of the surgical robotic system 10. As each of the carts 60*a-d* and/or robotic arms 40*a-d* is connected to the control tower 20, at step 202, the user may be prompted to select a color from a plurality of colors (e.g., a color palette) representing each of the carts 60*a-d*. Once selected, the color is then used in the GUI 150 as well as to color corresponding foot pedals 36. The control tower 20, and in particular the controller 21 assigns one or more pedals 36 to each of the robotic arms 40*a-d*. The color may be set based on the type of the attached instrument 50, e.g., purple for grasper, blue for scissors, pink for vessel sealer, etc. The color of the color indicators 102*a-d* and the GUI 150 may be changed during the surgical procedure. In embodiments, the color may be changed based on the phase of the surgery that is being performed. Phase determination could be based on image-processing based algorithms monitoring the video feed of the surgical site. In further embodiments, rather than using a single color, various color animations or combinations of colors may be used. The color indicators 102*a-d* may be turned on/off to display a moving pattern in the lights.

Each of the movable carts 60*a-d* is then positioned at step 204 around the surgical table 100 as described above. Once positioning is confirmed, at step 206 the GUI 150, including the graphical representations 152*a-d* and the orientation indicator 160, adopts the colors of the color indicators 102*a-d* allowing for cross-reference by the surgical personnel. In addition, at step 208 the color indicators 37 of the foot pedals 36 as selected by the controller 21 also adopt the corresponding color of one of the color indicators 102*a-d* to allow for matching the foot pedals 36 to one of the corresponding robotic arms 40*a-d*.

It will be understood that various modifications may be made to the aspects disclosed herein. In aspects, the color-coded relative position, angular orientation, and operational status of each robotic arm may also be simultaneously viewable on multiple displays. Therefore, the above description should not be construed as limiting, but merely as exemplifications of various aspects. Those skilled in the art will envision other modifications within the scope and spirit of the claims appended thereto.

What is claimed is:

1. A surgical robotic system comprising:

a plurality of movable carts each of the movable carts including a robotic arm and a cart color indicator configured to display a unique color identifying each movable cart among the plurality of movable carts; and a surgeon console including:

a display configured to display a graphical user interface having a plurality of graphical representations each of which corresponds to one movable cart of the plurality of movable carts, wherein each of the graphical representations displays the unique color of the cart color indicator of the corresponding movable cart to identify the corresponding movable cart among the plurality of movable carts; and a plurality of foot pedals configured to control the robotic arms, each of the plurality of foot pedals including a pedal color indicator, wherein each of the pedal color indicators is configured to display the unique color of the cart color indicator of a movable cart based on a foot pedal assignment to identify the movable cart assigned to the foot pedal.

2. The surgical robotic system according to claim 1, wherein each of the cart color indicator and the pedal color indicator includes at least one light emitting diode.

3. The surgical robotic system according to claim 1, further comprising:

a control tower coupled to the surgeon console and the plurality of movable carts, wherein the control tower is configured to control the robotic arm of each movable cart of the plurality of movable carts based on a user input received at the surgeon console.

4. The surgical robotic system according to claim 3, wherein the control tower is configured to assign the unique color to each of the cart color indicators.

5. The surgical robotic system according to claim 4, wherein the control tower is configured to assign the unique color to each of the cart color indicators based on a user selection.

6. The surgical robotic system according to claim 1, wherein the display is a touchscreen and each graphical representation of the plurality of graphical representations is movable on the touchscreen.

7. A surgical robotic system comprising:

a plurality of movable carts each including a robotic arm and a cart color indicator configured to display a unique color identifying each movable cart among the plurality of movable carts; and a surgeon console including a display configured to display a graphical user interface having a plurality of graphical representations each of which corresponds to one movable cart of the plurality of movable carts, wherein each of the graphical representations displays the unique color of the cart color indicator of the corresponding movable cart to identify the corresponding movable cart among the plurality of movable carts.

8. The surgical robotic system according to claim 7, wherein the cart color indicator includes at least one light emitting diode.

9. The surgical robotic system according to claim 7, wherein the surgeon console further includes a plurality of foot pedals configured to control the robotic arms.

10. The surgical robotic system according to claim 9, wherein each of the plurality of foot pedals includes a pedal color indicator.

11. The surgical robotic system according to claim 10, wherein each of the pedal color indicators is configured to display the unique color of the cart color indicator of a movable cart based on a foot pedal assignment.

12. The surgical robotic system according to claim 10, wherein the pedal color indicator includes at least one light emitting diode.

13. The surgical robotic system according to claim 10, further comprising:

a controller coupled to the surgeon console and the plurality of movable carts, wherein the controller is configured to control the robotic arm of each movable cart of the plurality of movable carts based on a user input received at the surgeon console.

14. The surgical robotic system according to claim 13, wherein the controller is configured to assign the unique color to each of the cart color indicators.

15. The surgical robotic system according to claim 14, wherein the controller is configured to assign the unique color to each of the cart color indicators based on a user selection.

16. The surgical robotic system according to claim 7, wherein the display is a touchscreen and each graphical representation of the plurality of graphical representations are movable on the touchscreen.

17. The surgical robotic system according to claim 7, wherein at least one movable cart of the plurality of movable carts includes an instrument drive unit and an instrument coupled to the instrument drive unit and the cart color indicator is disposed on at least one of the at least one movable cart, the instrument drive unit, or the instrument.

18. A method for controlling a surgical robotic system, the method comprising:

selecting a unique color for each cart color indicator of a movable cart of a plurality of movable carts, the unique color identifying each movable cart among the plurality of movable carts; and outputting on a display of a surgeon console a graphical user interface including a plurality of graphical representations each of which corresponds to one movable cart of the plurality of movable carts, wherein each of the graphical representations displays the unique color of the cart color indicator of the corresponding movable cart to identify the corresponding movable cart among the plurality of movable carts.

19. The method according to claim 18, further comprising:

assigning at least one pedal to each robotic arm, each of which is disposed on one movable cart of the plurality of carts.

20. The method according to claim 19, further comprising:

displaying on a pedal color indicator the unique color of the cart color indicator of a movable cart based on a foot pedal assignment.

* * * * *